(12) United States Patent
Lacey (10) Patent No.: US 7,201,515 B2
(45) Date of Patent: Apr. 10, 2007

(54) SYSTEM AND METHOD FOR COOLING COMPONENTS ROTATABLE ABOUT AN AXIS

(75) Inventor: Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/087,932

(22) Filed: Mar. 23, 2005

(65) Prior Publication Data

US 2006/0215808 A1    Sep. 28, 2006

(51) Int. Cl.
*H01J 35/10* (2006.01)
(52) U.S. Cl. .................... 378/199; 378/200
(58) Field of Classification Search ............ 378/4, 378/19, 15, 141, 199, 200
See application file for complete search history.

(56) References Cited

U.S. PATENT DOCUMENTS

| | | | |
|---|---|---|---|
| 3,865,182 A * | 2/1975 | Blossom .................. 165/245 |
| 4,969,167 A | 11/1990 | Zupancic et al. |
| 5,299,249 A | 3/1994 | Burke et al. |
| 5,610,968 A | 3/1997 | Deucher et al. |
| 6,411,672 B1 * | 6/2002 | Sasaki et al. ............... 378/19 |
| 6,988,827 B2 * | 1/2006 | Mueller .................... 378/199 |
| 2004/0202287 A1 * | 10/2004 | Muller ..................... 378/199 |

* cited by examiner

*Primary Examiner*—Edward J. Glick
*Assistant Examiner*—Irakli Kiknadze
(74) *Attorney, Agent, or Firm*—Carl B. Horton, Esq.; Armstrong Teasdale LLP

(57) ABSTRACT

Systems and methods for cooling electronic components that are rotatable about an axis are provided. The system includes a stationary portion, a rotatable portion, and a component cooling system. The stationary portion has a bore there through. The rotatable portion is rotatably coupled to the stationary portion. The rotatable portion includes an imaging detector and an associated electronic component. The component cooling system is positioned at least partially within the stationary portion and configured to channel a curtain of conditioned air to the electronic component.

22 Claims, 9 Drawing Sheets

Section View

Side View

Section View

Side View

SYSTEM AND METHOD FOR COOLING COMPONENTS ROTATABLE ABOUT AN AXIS

BACKGROUND OF THE INVENTION

The invention relates generally to cooling components of a medical imaging device, and more particularly, to cooling components of a medical imaging device that are rotatable about an axis.

A medical imaging device such as a Computed Tomography (CT), or a Positron Emission Tomography (PET) system, is used to generate images of body parts. The CT system includes an annular gantry that receives a patient within a gantry bore and rotates about the patient. The gantry includes an X-ray source to project a fan shaped X-ray beam extending along the plane of rotation of the gantry toward the bore. The X-ray beam passes through the patient where it is then received by a detector array. The detector array is held on the gantry opposite to the X-ray source with respect to the bore. The detector array receives the X-rays that pass through the patient's body. As a result, raw data is acquired by the detector array in response to the received X-rays.

The gantry of the CT system includes electronic components, which help in the data acquisition process. These electronic components control the rotation of the gantry, tilting of the gantry for angled images, and other functions such as turning the X-ray beam ON and OFF.

The electronic components and the detector array may be temperature sensitive. Hence, in typical CT systems, thermal controls may be utilized to prevent image quality errors due to temperature drift. Further, the electronic components and X-ray tube generate significant heat, which may cause air temperature to rise inside the gantry, thereby leading to temperature drift.

In particular, during a scanning operation, the air temperature inside the gantry may change by several degrees in a matter of seconds. In addition, variation in a temperature of a room, where the CT system is installed, may also cause changes in the gantry air temperature.

Additionally, in current CT systems, the electronic components may be placed closer to the highly temperature sensitive X-ray detector, in order to reduce circuit noise thereby increasing the signal to noise ratio. This causes the cooling and temperature control of the electronics to directly impact the control of the sensitive X-ray detector.

BRIEF DESCRIPTION OF THE INVENTION

In one exemplary embodiment, a method for cooling an electronic component that is rotatable about an axis is provided. The method includes receiving a flow of fluid from an ambient space, channeling the flow of fluid through a duct that extends circumferentially about the axis, and directing the flow of fluid axially towards the component.

In another exemplary embodiment, a medical imaging device gantry is provided. The medical imaging device gantry includes a stationary portion, a rotatable portion, and a component cooling system. The stationary portion has a bore there through. The rotatable portion is rotatably coupled to the stationary portion. The rotatable portion includes an imaging detector and an associated electronic component. The component cooling system is positioned at least partially within the stationary portion and configured to channel a curtain of conditioned air to the electronic component.

DETAILED DESCRIPTION OF THE INVENTION

Various embodiments of the invention provide methods and systems for cooling components that are rotatable about an axis. The method of cooling the components includes receiving a flow of fluid from an ambient space, channeling the flow of fluid through a duct that extends circumferentially about the axis, and directing the flow of fluid axially towards the component. The system provided by the invention is a medical imaging device gantry. The medical imaging device gantry includes a stationary portion comprising a bore, a rotatable portion that is coupled to the stationary portion, and a component cooling system positioned at least partially within the stationary portion. The component cooling system is configured to channel a curtain of conditioned air to the electronic component.

An example of a medical imaging device may be a CT system, or a Positron Emission Tomography (PET) system.

Figure 1:
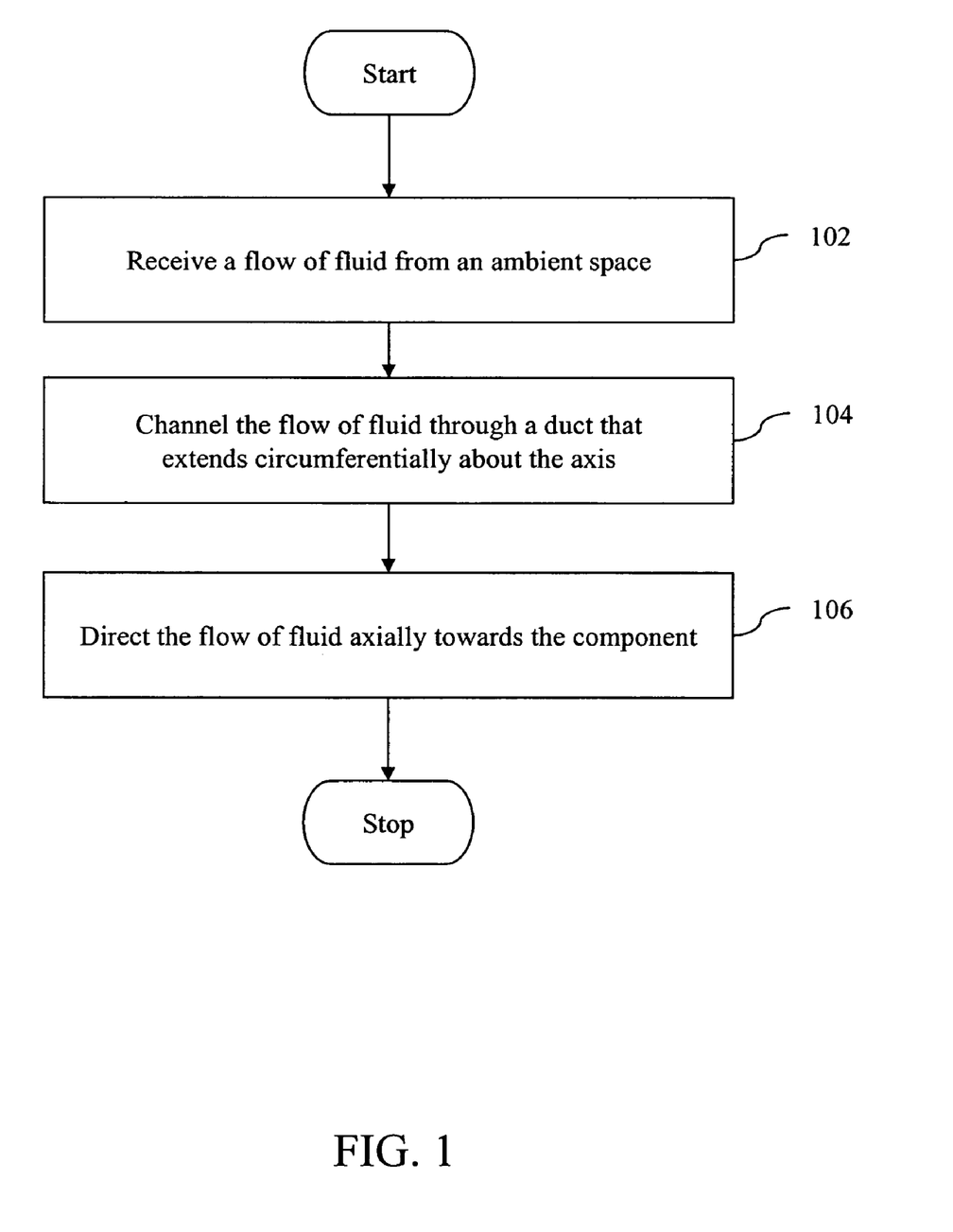
FIG. 1 is a flowchart depicting a method performed for cooling a component that is rotatable about an axis, in accordance with an exemplary embodiment of the invention.

FIG. 1 is a flowchart depicting a method performed for cooling a component that is rotatable about an axis, in accordance with an exemplary embodiment of the invention. At 102, flow of fluid from an ambient space is received. In an embodiment of the invention, the fluid may be air in the ambience. In other embodiments of the invention, other fluids may be used such as inert gases, nitrogen, and carbon dioxide.

At 104, the flow of the fluid is channeled through a duct that extends circumferentially about the axis. The duct is parallel to the axis. In an embodiment of the invention, there are multiple ducts that extend circumferentially about the axis. At 106, the flow of fluid is directed axially towards the component. As a result, the fluid exchanges heat with the component. This results in the component temperature to reduce. In this manner, the fluid in the ambient space is utilized to cool the component. The method of cooling a component that is rotatable about an axis is described in detail, in conjunction with FIG. 2. In another embodiment of the invention, the fluid may be utilized to heat the component if required. In such a case, the component may be at a lower temperature than required, and the fluid may be at a higher temperature. Hence, directing a flow of the fluid towards the component at a lower temperature results in raising the temperature of the component.

Figure 2:
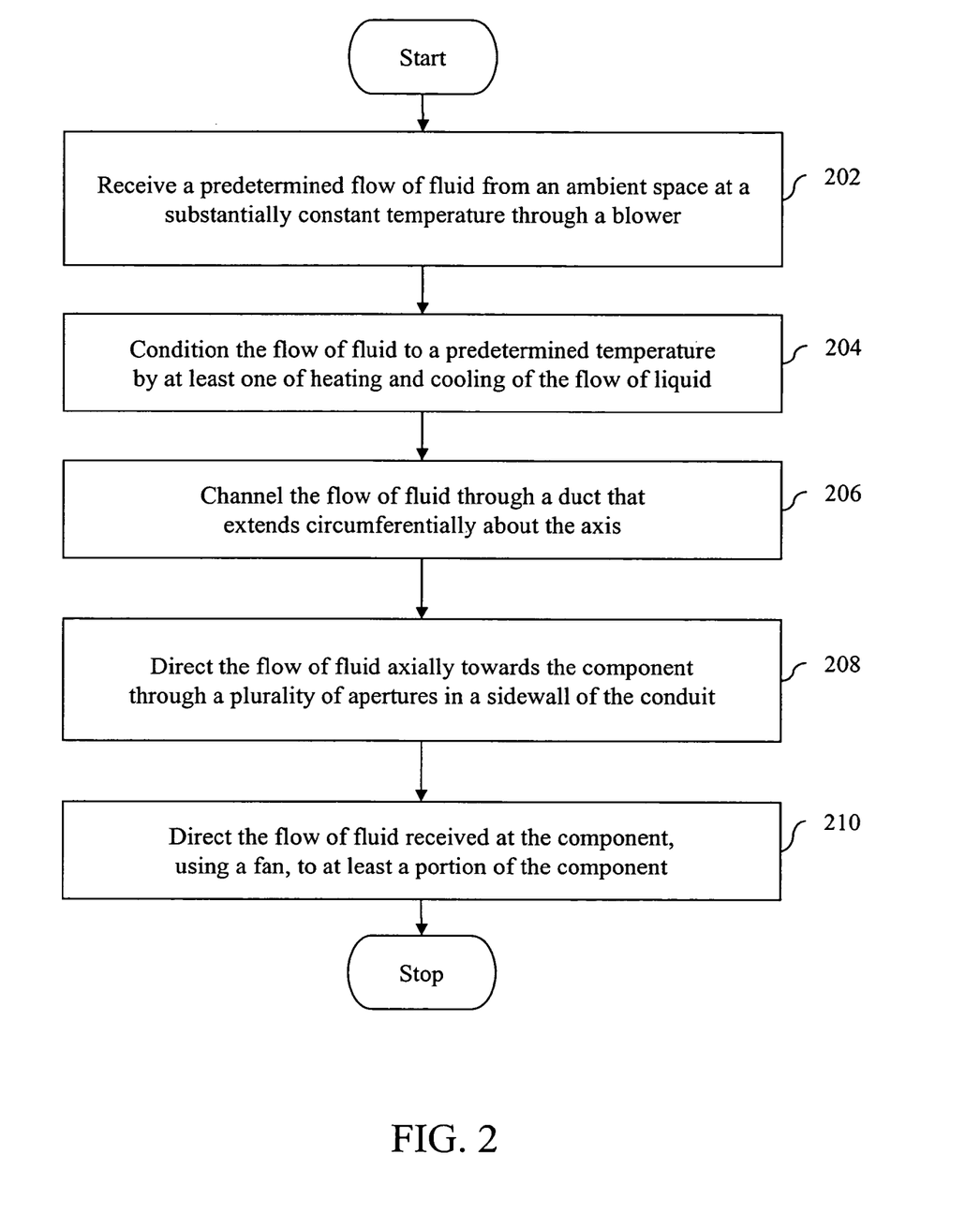
FIG. 2 is a flowchart depicting a method performed for cooling a component that is rotatable about an axis, in accordance with another exemplary embodiment of the invention.

FIG. 2 is a flowchart depicting a method performed for cooling a component that is rotatable about an axis, in accordance with another exemplary embodiment of the invention. At 202, a predetermined flow of fluid is received at a substantially constant temperature from ambient space through a blower. Further, channeling the flow of fluid through one of a heat exchanger and heating element achieves the substantially constant temperature. The predetermined flow of liquid is determined by computing the amount of fluid that may be required to control the temperature within a range. At 204, at least one of heating and cooling of the flow of liquid conditions the flow of fluid. In this process, the fluid gets either heated or cooled depending on the requirement. In an embodiment of the invention, flow of fluid, received at the component, is directed towards at least a portion of the component such that the portion of the component is maintained at a predetermined temperature range. At 206, the flow of fluid is channeled through the duct that extends circumferentially about the axis. In an embodiment of the invention, the flow of the liquid is directed axially through a plurality of apertures in a sidewall of the conduit. The apertures are configured to generate a substantially circumferentially continuous curtain of fluid coaxial with the axis. At 208, the flow of fluid is directed axially towards the component through a plurality of apertures in a sidewall of a, conduit that are spaced circumferentially about the axis. Thereafter, at 210, the flow of fluid received at the component, is directed to at least a portion of the component, using a fan.

In an embodiment of the invention, the method of cooling the components is carried out in a medical imaging device gantry. The medical imaging device gantry is described in detail, in conjunction with FIG. 3.

Figure 3:
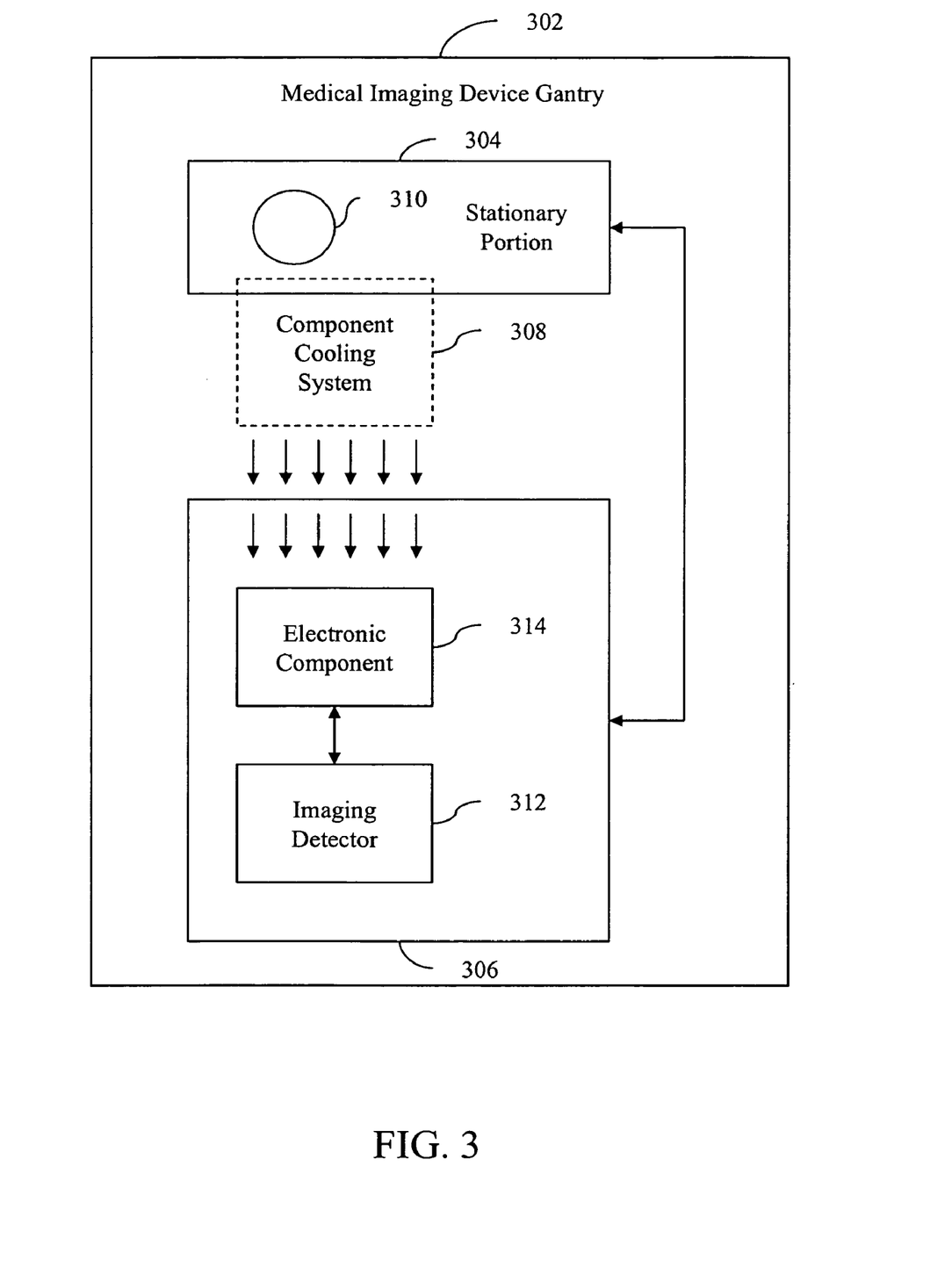
FIG. 3 is a block diagram illustrating various elements of a medical imaging device gantry, in accordance with an exemplary embodiment of the invention.

FIG. 3 is a block diagram illustrating various elements of a medical imaging device gantry 302, in accordance with an exemplary embodiment of the invention. Medical imaging device gantry 302 comprises a stationary portion 304, a rotatable portion 306, and a component cooling system 308. Stationary portion 304 comprises a bore 310 that runs through stationary portion 304. Rotatable portion 306 is rotatably coupled to stationary portion 304. Rotatable portion 306 comprises an imaging detector 312, and an electronic component 314. Electronic component 314 is associated with imaging detector 312. In an embodiment of the invention, electronic component 314 translates the output of imaging detector 312 to an electrical signal that may be transmitted over to a computer for further analysis for generation of images. Electronic component 314 is described in detail, in conjunction with FIG. 7.

Component cooling system 308 is positioned at least partially within stationary portion 304 and is configured to channel a curtain of conditioned air to electronic component 314. In an embodiment of the invention, component cooling system 308 may be a fan that channels the curtain of air towards electronic component 314. In another embodiment, component cooling system 308 may be a nozzle that channels the curtain of air towards electronic component 314. Component cooling system 308 is described in detail, in conjunction with FIG. 5.

Figure 4:
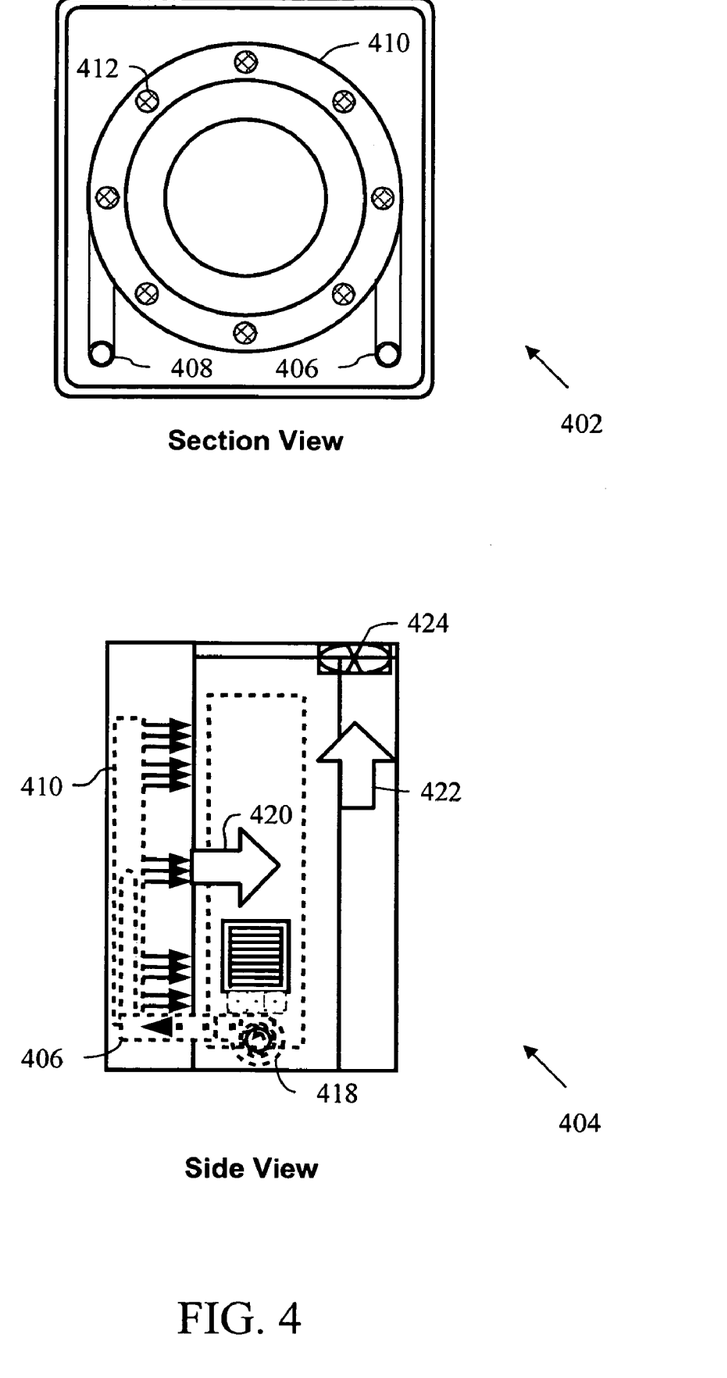
FIG. 4 is a block diagram illustrating various elements of a medical imaging device gantry, in accordance with another exemplary embodiment of the present invention.

FIG. 4 is a block diagram illustrating various elements of a medical imaging device gantry, in accordance with another exemplary embodiment of the present invention. FIG. 4 depicts two views, i.e., a sectional view 402 and a side view 404 of the medical imaging device gantry. In sectional view 402, an intake duct 406 and an intake duct 408 are shown along with a ring shaped plenum 410 and a plenum outlet vent 412. As seen in FIG. 4, plenum outlet vents similar to plenum outlet vent 412 are present all over the periphery of ring shaped plenum 410. Air intake is done through intake ducts 406 and 408.

In side view 404, intake duct 406, ring shaped plenum 410, a blower 418, a cool airflow 420, a hot airflow 422, and a hot air exhaust 424 may be seen. Blower 418 is used for intake of air through intake duct 406. Cool airflow 420 depicts the direction of flow of cold air inside the medical device gantry, while hot airflow 422 depicts the direction of flow of hot air inside the medical imaging device gantry. Hot air exhaust 424 is used for the exhaust of hot air from the medical imaging device gantry.

Figure 5:
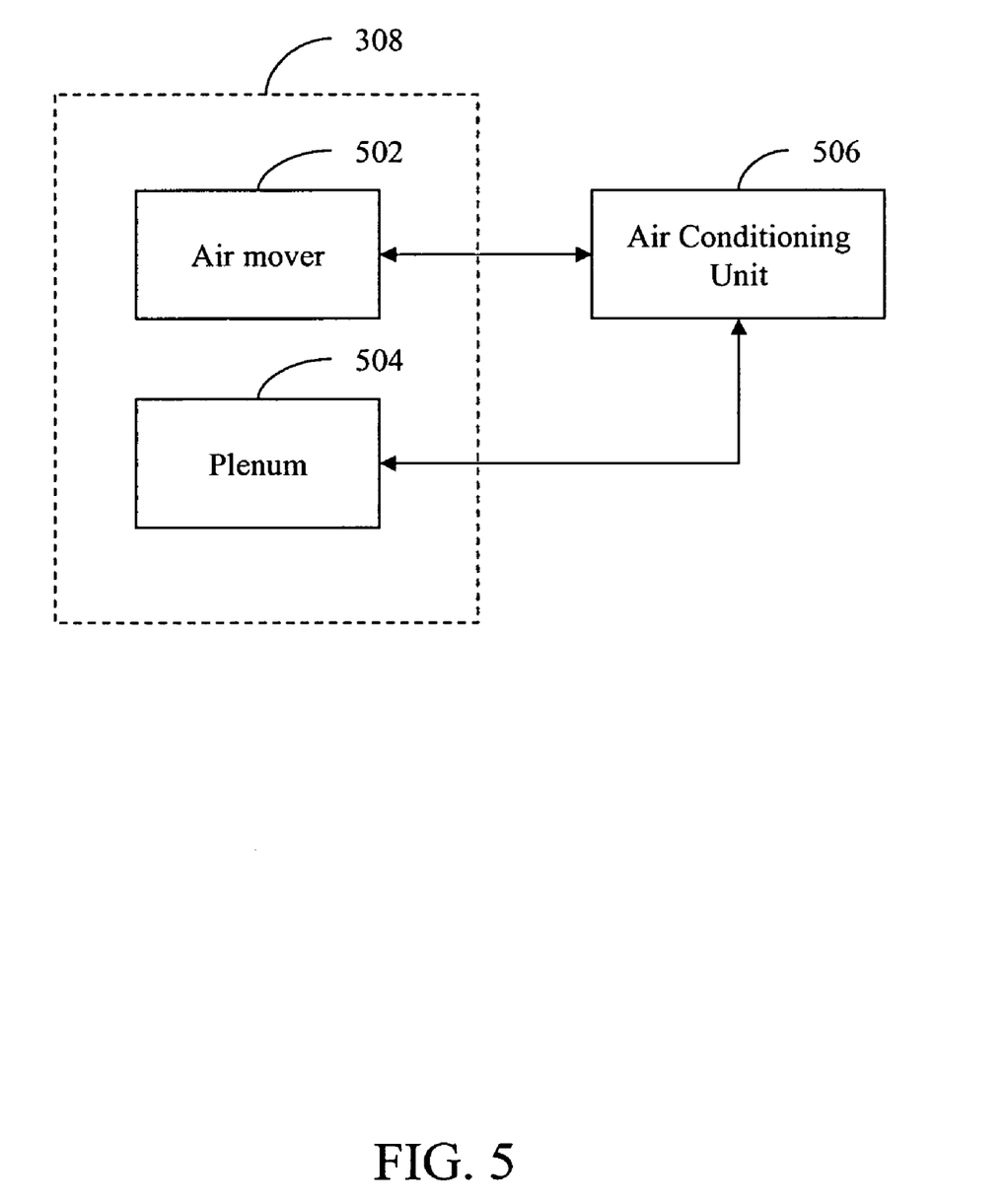
FIG. 5 is a block diagram illustrating various components of a component cooling system, in accordance with an exemplary embodiment of the invention.

FIG. 5 is a block diagram illustrating various components of component cooling system 308, in accordance with an exemplary embodiment of the invention. Component cooling system 308 comprises an air mover 502 and a plenum 504. Air mover 502 is configured to channel air from the ambient space surrounding the gantry to an air conditioning unit 506. Plenum 504 is coupled to air conditioning unit 506. Plenum 504 circumscribes bore 310. Plenum 504 is configured to distribute at least portion of the conditioned air circumferentially about bore 310. Plenum 504 is described in detail, in conjunction with FIG. 6.

In an embodiment, a heating element is provided in an inlet duct. In another embodiment, a heat-exchanging element is provided in the inlet duct. Heating or cooling of the feed, i.e., intake air of any other fluid may be done in the heat-exchanging element by an outside air conditioning unit.

Figure 6:
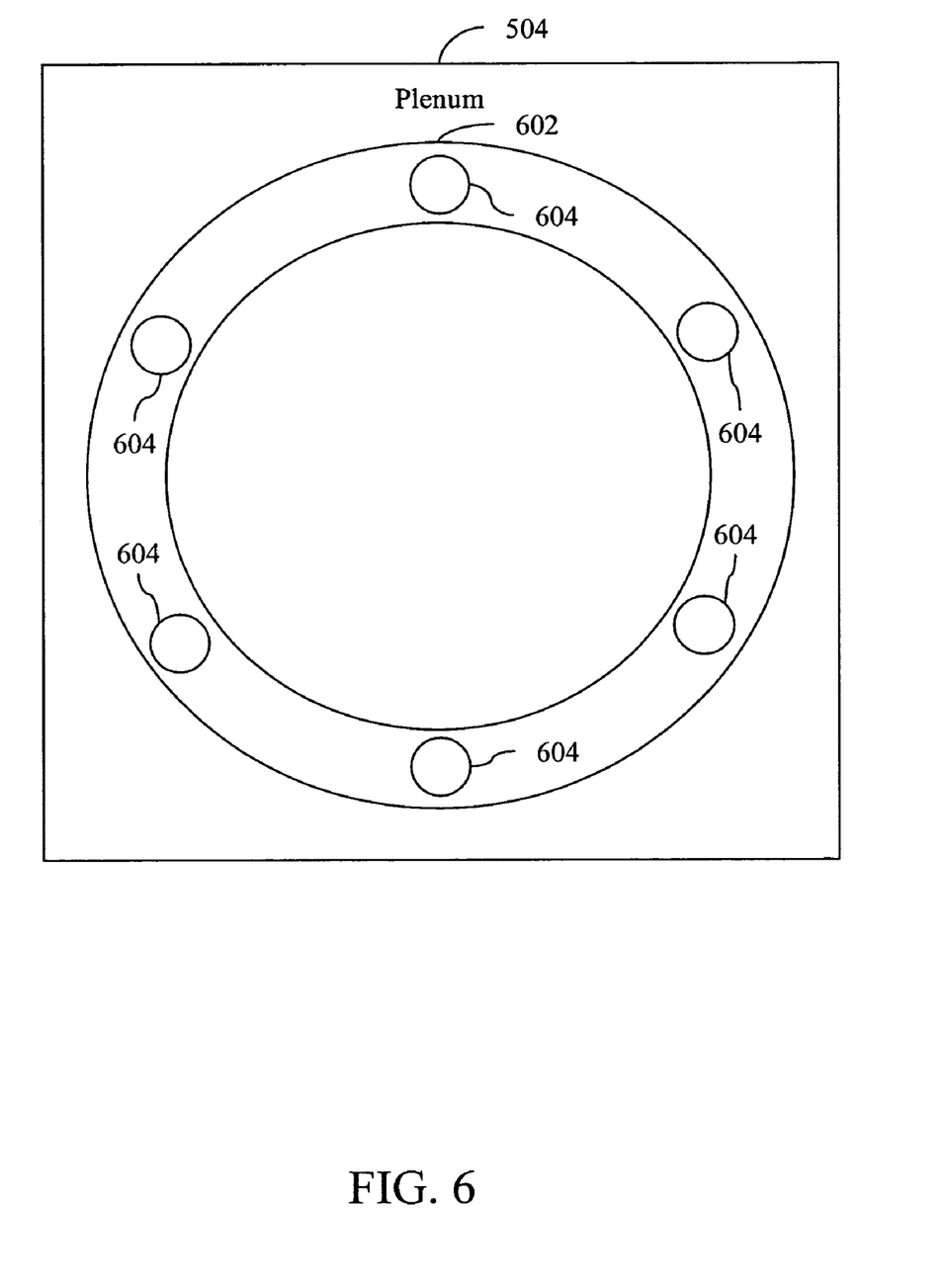
FIG. 6 is a sketch of a plenum, in accordance with an exemplary embodiment of the invention.

FIG. 6 is a sketch of plenum 504, in accordance with an exemplary embodiment of the invention. Plenum 504 comprises an arcuate conduit 602. Arcuate conduit 602 comprises at least one aperture 604 that is spaced circumferentially about a sidewall of arcuate conduit 602. In an embodiment of the invention, imaging detector 312 is moving in a rotational path about the axis, and the sidewall of arcuate conduit 602 is adjacent to the rotational path. At least one aperture 604 is configured to distribute at least portion of the conditioned air in a substantially cylindrically shaped air curtain into the rotational path of imaging detector 312.

Figure 7:
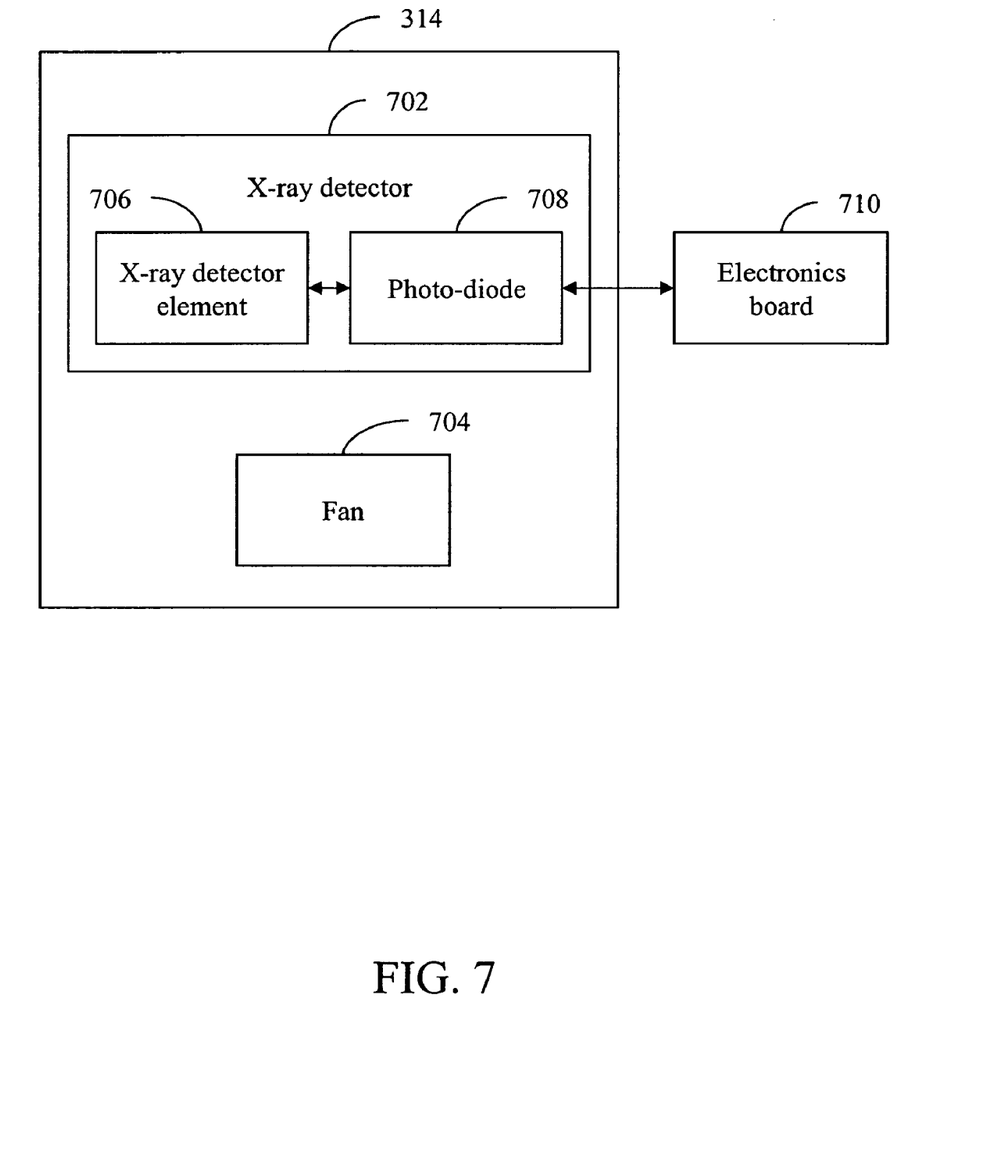
FIG. 7 is a block diagram illustrating an electronic component, in accordance with an exemplary embodiment of the invention.

FIG. 7 is a block diagram illustrating electronic component 314, in accordance with an exemplary embodiment of the invention. Electronic component 314 comprises an X-ray detector 702, and a fan 704. Fan 704 is configured to direct the distributed air to X-ray detector 702. X-ray detector 702 includes an X-ray detector element 706 and a photo diode 708. In an embodiment of the invention, fan 704 is configured to facilitate in maintaining photo diode 708 at a temperature within a predetermined temperature range.

X-ray detector element 706 is coupled in photo communication with photo diode 708. Photo diode 708 is communicatively coupled to an electronics board 710. In an embodiment of the invention, the communication between photo diode 708 and electronics board 710 is achieved by means of an electrical cable.

Figure 8:
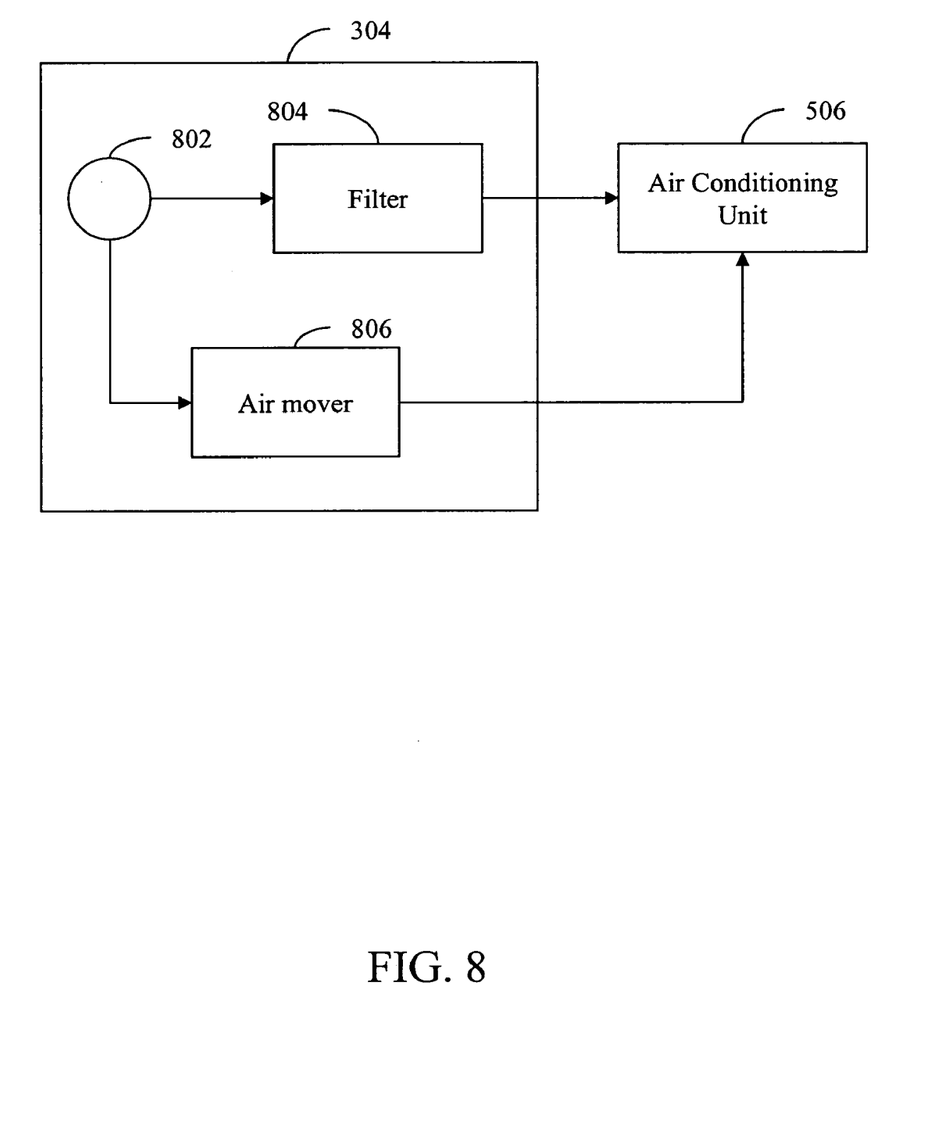
FIG. 8 is a block diagram illustrating a stationary portion of a medical imaging device gantry, in accordance with an exemplary embodiment of the invention.

FIG. 8 is a block diagram illustrating stationary portion 304 of a medical imaging device gantry, in accordance with an exemplary embodiment of the invention. Stationary portion 304 includes an ambient air inlet aperture 802, a filter 804, and an air mover 806. Filter 804 is coupled in flow communication between ambient air inlet aperture 802 and air conditioning unit 506. Filter 804 is an air filter that is utilized to remove the impurities such as dust that may impair the correct operation of components inside the gantry. Air mover 806 is configured to channel air from ambient air inlet aperture 802 to air conditioning unit 506.

Figure 9:
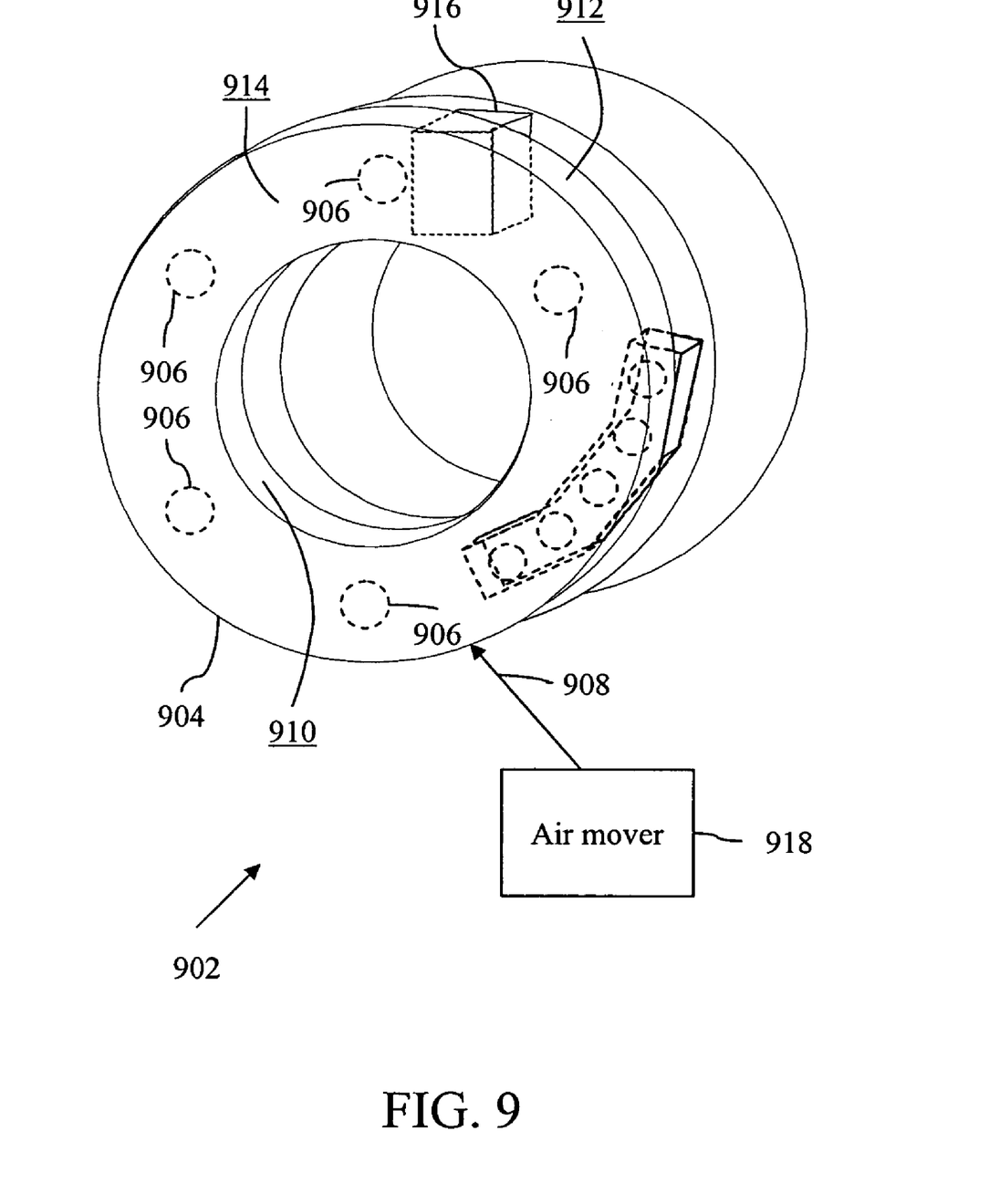
FIG. 9 illustrates a medical imaging device cooling duct, in accordance with an exemplary embodiment of the invention.

FIG. 9 illustrates a medical imaging device cooling duct 902, in accordance with an exemplary embodiment of the invention. Medical imaging device cooling duct 902 includes a ring shaped conduit 904, an aperture 906 and an inlet 908. Ring shaped conduit 904 includes a radially inner peripheral portion 910, a radially outer peripheral portion 912 and a sidewall 914. Sidewall 914 extends between radially inner peripheral portion 910 and radially outer peripheral portion 912.

Aperture 906 extends through sidewall 914 and is configured to direct the flow of air axially towards a rotational path of a detector 916. Inlet 908 is configured to channel flow of air from an air mover 918 into ring shaped conduit 904.

In an embodiment of the invention, aperture 906 includes a slot that extends circumferentially about at least a portion of ring shaped conduit 904. In an embodiment of the invention, the slot is sized to regulate the flow of air from the slot. The width of the slot is sized to circumferentially balance the flow of air from the slot.

In an embodiment of the invention, a plurality of apertures is circumferentially spaced about at least a portion of ring shaped conduit 904. Each of the apertures is sized so as to regulate the flow of air. Each aperture is sized in a manner so as to permit a flow of air that is substantially equal to the flow of air from other apertures.

Various embodiments of the present invention provide systems and methods for cooling components that are rotatable about an axis. In an embodiment of the invention, a system and a method to cool the electronic components inside a gantry of a CT system are provided. The system may be utilized to either cool or heat the electronic components depending on the requirement. An embodiment of the invention reduces the cost of cooling the electronic components in the gantry, as the invention does not require a totally air-conditioned gantry.

While the invention has been described in terms of various specific embodiments, those skilled in the art will recognize that the invention can be practiced with modification within the spirit and scope of the claims.

What is claimed is:

1. A method for cooling a component that is rotatable about an axis, said method comprising:
   receiving a flow of fluid from an ambient space;
   channeling the flow of fluid through a conduit that extends circumferentially about the axis; and
   directing the flow of fluid axially towards the component through a plurality of apertures spaced circumferentially about the axis in a sidewall of the conduit, wherein the plurality of apertures are configured to generate a substantially circumferentially continuous curtain of fluid coaxial with the axis.

2. A method in accordance with claim 1 further comprising conditioning the flow of fluid to a predetermined temperature.

3. A method in accordance with claim 2 wherein conditioning the flow of fluid to a predetermined temperature comprises at least one of heating and cooling the flow of fluid to the predetermined temperature.

4. A method in accordance with claim 1 further comprising receiving the flow of fluid, at the component, at a substantially constant predetermined temperature.

5. A method in accordance with claim 1 further comprising directing the flow of fluid, received at the component, towards at least a portion of the component such that the portion of the component is facilitated being maintained within a predetermined temperature range.

6. A method in accordance with claim 5 wherein directing the flow of fluid, received at the component, comprises using a fan to direct the flow of fluid towards a portion of the component.

7. A method in accordance with claim 1 wherein receiving a flow of fluid from an ambient space comprises receiving a predetermined flow of fluid from the ambient space through a blower.

8. A method in accordance with claim 1 wherein receiving a flow of fluid from an ambient space comprises channeling a predetermined flow of fluid from the ambient space to a heat exchanger.

9. A method in accordance with claim 1 wherein receiving a flow of fluid from an ambient space comprises channeling a predetermined flow of fluid from the ambient space to a heating element.

10. A method in accordance with claim 1 further comprising rotating the component about the axis on an arcuate path substantially coincident with the curtain of fluid.

11. A medical imaging device gantry comprising:
    a stationary portion comprising a bore therethrough;
    a rotatable portion rotatably coupled to said stationary portion, said rotatable portion comprising an imaging detector and an associated electronic component; and
    a component cooling system comprising an arcuate conduit positioned at least partially within said stationary portion and surrounding at least a portion of said bore, said component cooling system configured to:
    receive a flow of fluid from an ambient space;
    condition the received flow of fluid; and
    channel a substantially cylindrically-shaped curtain of conditioned air through said arcuate conduit toward a rotational path of said imaging detector.

12. A medical imaging device gantry in accordance with claim 11 wherein said component cooling system further comprises:
    an air mover configured to channel air from an ambient space surrounding said medical imaging device gantry to an air conditioning unit; and
    a plenum coupled to said air conditioning unit, said plenum circumscribing said bore and said arcuate conduit, said plenum configured to distribute at least a portion of the conditioned air circumferentially about said bore and said arcuate conduit.

13. A medical imaging device gantry in accordance with claim 12 wherein said arcuate conduit comprises a plurality of apertures spaced circumferentially about a sidewall of the arcuate conduit, said sidewall is adjacent to the rotational path of said imaging detector.

14. A medical imaging device gantry in accordance with claim 11 wherein said electronic component comprises an x-ray detector and a fan configured to direct the distributed air to said x-ray detector, said x-ray detector comprising an x-ray detector element coupled in photo communication with a photo diode, said photo diode communicatively coupled to an electronics board.

15. A medical imaging device gantry in accordance with claim 14 wherein said fan is configured to facilitate maintaining said photo diode at a temperature within a predetermined temperature range.

16. A medical imaging device gantry in accordance with claim 11 wherein said stationary portion comprises an ambient air inlet aperture, a filter coupled in flow communication between said ambient air inlet aperture and an air conditioning unit, and an air mover configured to channel air from said ambient air inlet aperture to said air conditioning unit.

17. A medical imaging device cooling duct comprising:
- a ring-shaped conduit configured to circumscribe a longitudinal axis of a viewing area bore of the medical imaging device, said conduit comprising a radially inner peripheral portion, a radially outer peripheral portion, and a sidewall extending therebetween;
- a plurality of apertures spaced circumferentially about at least a portion of said ring-shaped conduit, each aperture extending through said sidewall and configured to direct a flow of air axially toward a detector rotational path within said ring-shaped conduit; and
- at least one inlet configured to channel the flow of air from an ambient space into said ring-shaped conduit.

18. A medical imaging device cooling duct in accordance with claim 17 wherein at least one of said apertures comprises a slot that extends circumferentially about at least a portion of said ring-shaped conduit.

19. A medical imaging device cooling duct in accordance with claim 18 wherein said slot is sized to regulate the flow of air from the slot.

20. A medical imaging device cooling duct in accordance with claim 19 wherein a width of said slot is sized to circumferentially balance the flow of air from the slot.

21. A medical imaging device cooling duct in accordance with claim 17 wherein said plurality of apertures are each sized to regulate a flow of air from each aperture.

22. A medical imaging device cooling duct in accordance with claim 17 wherein said plurality of apertures are each sized to permit a flow of air from each aperture that is substantially equal to the flow of air from each other aperture.

* * * * *